United States Patent
Perry

(10) Patent No.: US 8,439,084 B2
(45) Date of Patent: *May 14, 2013

(54) FLEXIBLE CONDUIT WITH LOCKING ELEMENT

(75) Inventor: Stephen J. Perry, Shirley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/241,546

(22) Filed: Sep. 23, 2011

(65) Prior Publication Data

US 2012/0012220 A1  Jan. 19, 2012

Related U.S. Application Data

(63) Continuation of application No. 12/481,258, filed on Jun. 9, 2009, now Pat. No. 8,047,236.

(60) Provisional application No. 61/096,529, filed on Sep. 12, 2008.

(51) Int. Cl.
*F16L 27/04* (2006.01)

(52) U.S. Cl.
USPC ... 138/120; 138/155; 138/DIG. 8; 285/146.1; 285/264; 285/184; 239/587.1; 239/587.4

(58) Field of Classification Search .................. 138/120, 138/155, 109, 118, DIG. 8; 239/587.1–587.5, 239/588, 600; 285/146.1, 166, 264, 184

See application file for complete search history.

(56) References Cited

U.S. PATENT DOCUMENTS

| 4,516,972 | A | * | 5/1985 | Samson | 604/526 |
| 4,601,283 | A | * | 7/1986 | Chikama | 600/151 |
| 5,251,611 | A | * | 10/1993 | Zehel et al. | 600/141 |
| 5,320,843 | A | * | 6/1994 | Raheja et al. | 424/405 |
| 5,337,733 | A | * | 8/1994 | Bauerfeind et al. | 600/139 |
| 5,749,602 | A | * | 5/1998 | Delaney et al. | 285/61 |
| 5,779,624 | A | * | 7/1998 | Chang | 600/114 |
| 5,865,378 | A | * | 2/1999 | Hollinshead et al. | 239/587.1 |
| 5,997,047 | A | * | 12/1999 | Pimentel et al. | 285/55 |
| 6,554,820 | B1 | * | 4/2003 | Wendlandt et al. | 604/527 |
| 6,626,210 | B2 | * | 9/2003 | Luettgen et al. | 138/120 |
| 6,629,651 | B1 | * | 10/2003 | Male et al. | 239/587.1 |

(Continued)

OTHER PUBLICATIONS

International Search Report for related International Application No. PCT/US2009/050961, mailed Oct. 28, 2009.

*Primary Examiner* — Patrick F Brinson
(74) *Attorney, Agent, or Firm* — Bookoff McAndrews, PLLC

(57) ABSTRACT

A flexible conduit for insertion into a body lumen comprises a plurality of elements coupled end to end to define a conduit lumen. A first one of the elements includes a male portion and a female portion. A second element includes a female portion having an inner surface configured to engage a male portion of an outer surface of the first element to form a first ball joint. A third element includes a male portion, an outer surface of the male portion of the third element configured to engage an inner surface of the female portion of the first element to form a second ball joint. The male and female portions of the first element are adapted to frictionally engage the female portion of the second element and the male portion of the third element to establish a rigid connection therebetween.

15 Claims, 7 Drawing Sheets

U.S. PATENT DOCUMENTS

| | | | |
|---|---|---|---|
| 6,790,173 B2 * | 9/2004 | Saadat et al. | 600/114 |
| 6,793,621 B2 * | 9/2004 | Butler et al. | 600/114 |
| 7,066,411 B2 * | 6/2006 | Male et al. | 239/587.1 |
| 7,337,808 B2 * | 3/2008 | Shamir et al. | 138/120 |
| 7,533,906 B2 * | 5/2009 | Luettgen et al. | 285/146.1 |
| 8,047,236 B2 | 11/2011 | Perry | |
| 2004/0193008 A1 * | 9/2004 | Jaffe et al. | 600/114 |
| 2004/0199052 A1 * | 10/2004 | Banik et al. | 600/142 |
| 2005/0103903 A1 * | 5/2005 | Shamir et al. | 239/587.2 |
| 2006/0178560 A1 * | 8/2006 | Saadat et al. | 600/114 |

* cited by examiner

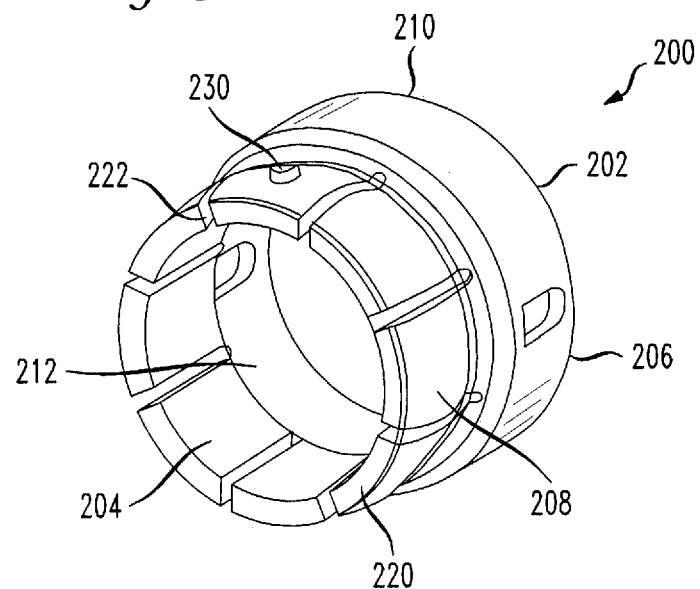
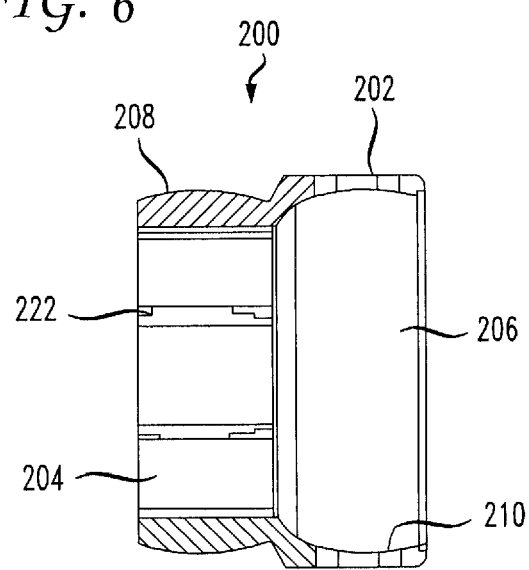

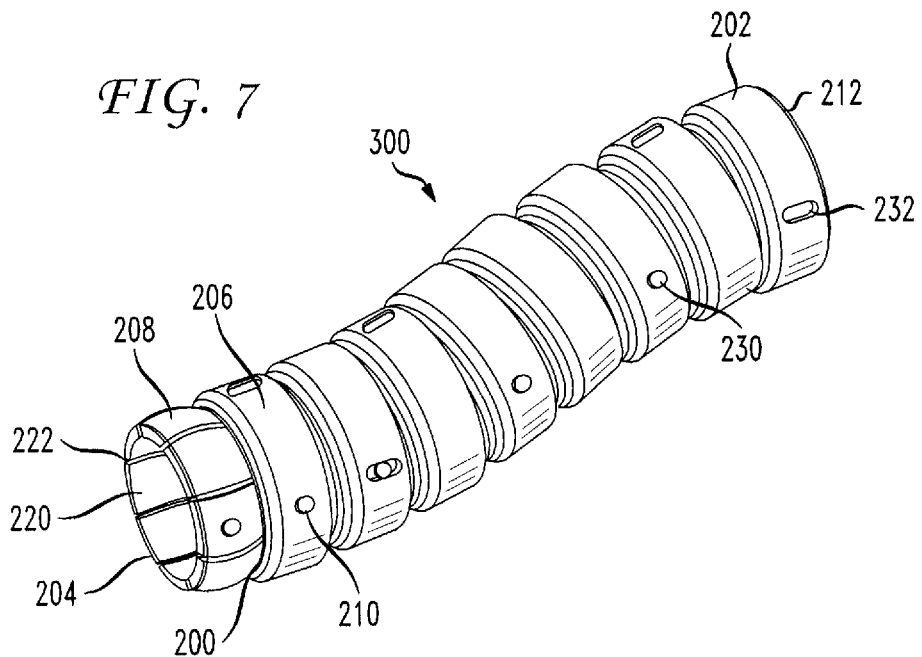
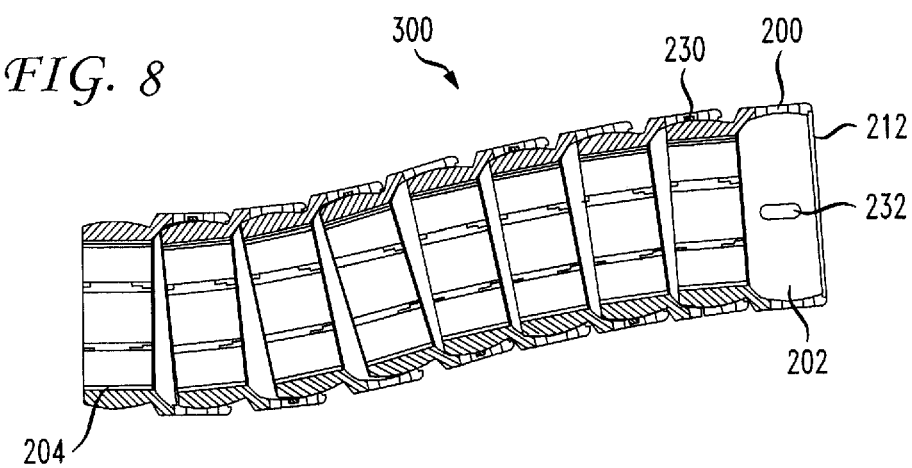
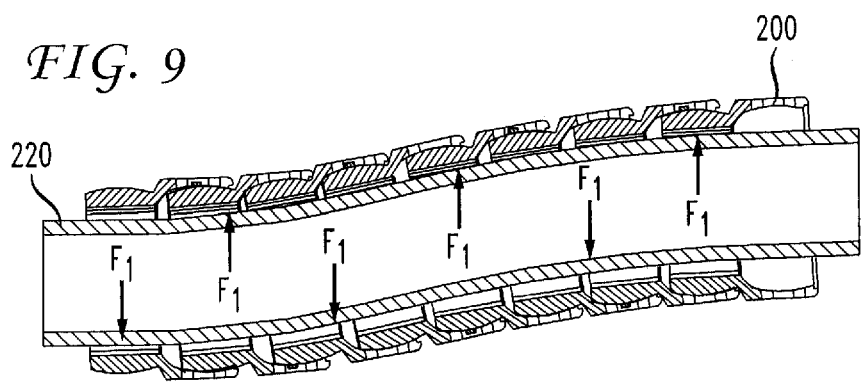

FLEXIBLE CONDUIT WITH LOCKING ELEMENT

PRIORITY CLAIM

This application is a continuation of application Ser. No. 12/481,258, filed Jun. 9, 2009, now U.S. Pat. No. 8,047,236 B2, which claims the benefit of U.S. Provisional Application No. 61/096,529, filed Sep. 12, 2008, all of which are incorporated herein by reference.

BACKGROUND

Many procedures for the exploration and treatment of the gastro-intestinal (GI) tract involve the insertion of an endoscope into the GI tract. During examinations, a user may navigate the GI anatomy using a steerable endoscopic tip, or alternatively by performing a series of torquing, pushing and pulling maneuvers at the proximal end of the device to advance and direct the distal end. The forces applied to the endoscope are transferred to the surrounding tissue and may be problematic and painful. Movement of the endoscope may cause spasms and may, in certain cases, even perforate the intestine. It is therefore necessary to perform the procedure slowly and at times, it may not be possible to reach remote areas without unduly traumatizing surrounding tissue.

Various guides have been developed in order to absorb this stress and facilitate insertion of the endoscope while minimizing the impact on the lumenal walls. However, the current guides are often expensive, bulky and/or require added steps which unduly complicate the procedures.

SUMMARY OF THE INVENTION

The present invention is directed to a flexible conduit for insertion into a body lumen, the conduit comprising a plurality of elements coupled end to end with lumens of the elements aligned to define a conduit lumen. The plurality of elements include a first element including a male portion and a female portion and a second element including a female portion having an inner surface extending along a curve corresponding to a curve of the male portion of an outer surface of the first element so that, when the male portion of the first element is received within the female portion of the second element, the first and second elements form a first ball joint. A third element includes a male portion, an outer surface of the male portion of the third element being curved along a shape corresponding to a curve of an inner surface of the female portion of the first element so that, when the male portion of the third element is received within the female portion of the first element, the first and third elements form a second ball and socket joint, the male and female portions of the first element being adapted to frictionally engage respectively, the female portion of the second element and the male portion of the third element to establish a rigidity of the conduit sufficient to retain its shape and absorb forces applied thereto as a flexible instrument is inserted through the conduit lumen.

BRIEF DESCRIPTION OF DRAWINGS

FIG. 5 is a perspective view showing an element of a flexible conduit according to a second embodiment of the invention;

FIG. 6 is a partial cross-sectional side view showing the element of FIG. 5;

FIG. 7 is a perspective view showing multiple connected elements of a flexible conduit according to a second embodiment of the invention;

FIG. 8 is a partial cross-sectional side view of the flexible conduit of FIG. 7;

FIG. 9 is another partial cross-sectional side view showing forces applied to the flexible conduit of FIG. 7;

DETAILED DESCRIPTION

Figure 1:
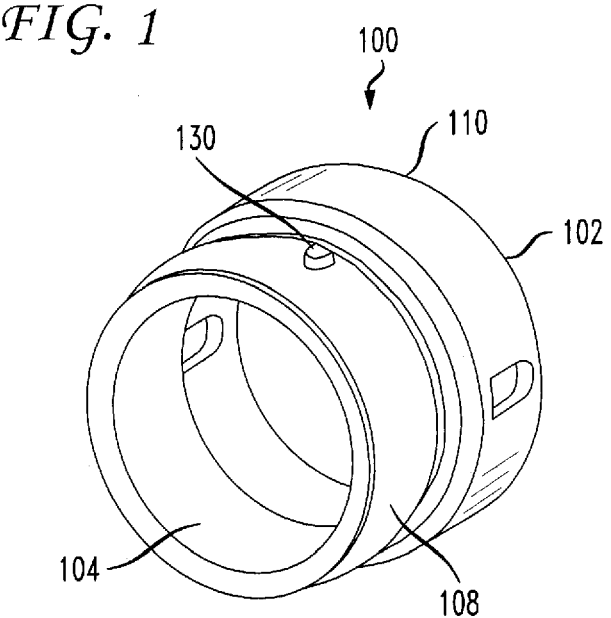
FIG. 1 is a perspective view showing an element of a flexible conduit according to a first embodiment of the invention.
Figure 2:
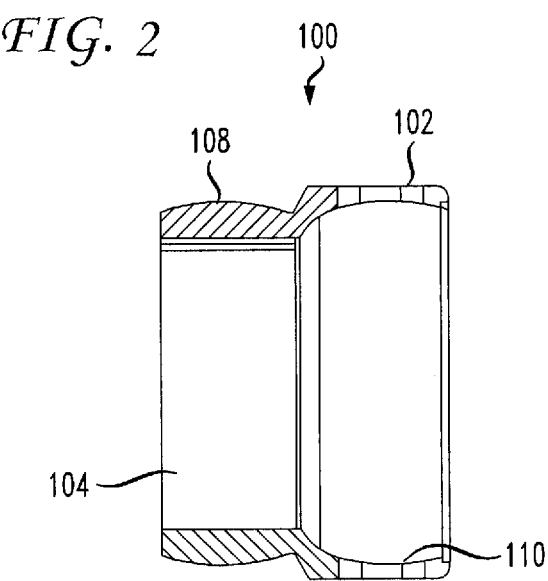
FIG. 2 is a partial cross-sectional side view of the element of FIG. 1.

The present invention may be further understood with reference to the following description and to the appended drawings, wherein like elements are referred to with the same reference numerals. The present invention relates to guides for the insertion of flexible endoscopes or other flexible elongate instruments along tortuous body lumen paths. The exemplary embodiments are described herein in conjunction with flexible endoscopes. However, those skilled in the art will understand that the guides may be used to facilitate the insertion of any flexible instrument through a body lumen and that the discussion of endoscopes is exemplary only and is not intended to limit the invention. For example, embodiments of the flexible instrument guide according to the invention may be used to improve colonoscopy, enteroscopy, exploration of the biliary tree, exploration of the GI tract and of extraluminal space, among others. These methods and devices are useful for screening and diagnostic purposes, as well as for the treatment of many conditions.

A guide according to the present invention is sufficiently longitudinally flexible to be inserted along a path defined by an endoscope while remaining sufficiently longitudinally plastically deformable to ease insertion through the endoscope without kinking, as those skilled in the art will understand. As the endoscope is inserted through the guide, the stress exerted outward from the endoscope to the body lumen is absorbed by the guide and is not transferred to surrounding tissue. The longitudinal rigidity of guides according to certain embodiments of the invention may be varied during the procedure so that the guide may be inserted and removed while in a more flexible state and rigidized when it has assumed a desired shape. The guides according to the invention are also preferably torsionally rigid to facilitate the placement of distal ends thereof at desired locations and/or in desired rotational orientations within the body. A working lumen extending through the guides is sized to allow passage therethrough of a flexible instrument to be used in accordance with an exemplary treatment procedure. Those skilled in the art will understand that, as used in this application, the term axial refers to a longitudinal axis of the conduit (i.e., a path along which one of the discrete elements of the conduit is situated) unless specifically defined otherwise.

As shown in FIGS. 1-4, a guide according to a first embodiment of the invention comprises a plurality of elements 100 connected together to form a conduit 150. Each of the elements 100 is substantially tubular and comprises a slotted portion with a curved outer surface formed of a unibody cylindrical disk, as will be described in greater detail hereinafter. Those skilled in the art will understand that, although the elements 100 are described as being substantially tubular, this refers to a shape of the elements 100 when linked together to form a conduit and does not require that the elements be strictly cylindrical. Generally, the elements 100 will have a substantially smooth, atraumatic outer surface with a cross-section which may be circular, elliptical or any other shape which facilitates the passing therethrough of selected instruments or which facilitates travel through target body lumens.

Each of the cylindrical elements 100 comprises a female portion 102 and a male portion 104 joined to one another. An inner surface 110 of the female portion 102 is sized and shaped to slidingly receive an outer surface 108 of the male portion 104 to form a ball and socket joint. That is, a curve of the inner surface 110 of the female portion 102 and a curve of the outer surface 108 of the male portion 104 are shaped and sized to closely fit one another while allowing for rotation about lines substantially perpendicular to the longitudinal axis of the element 100. For example, the surfaces 108 and 110 may form parts of spheres with a diameter of the inner surface 108 exceeding that of the outer surface 110 by a tolerance amount selected to maintain adjacent ones of the elements 100 bonded to one another while allowing the desired rotation and while providing a desired level of frictional engagement of the mated elements 100. As would be understood by those skilled in the art, the level of frictional engagement between adjacent elements 100 may be adjusted through material choice, setting of the tolerance between the surfaces 108 and 110 and by applying, for example, a surface treatment to all or parts of the surfaces 108 and 110. The desired level of frictional engagement is set to achieve a desired resistance to bending of the conduit 150 as an endoscope is inserted therethrough while maintaining a level of flexibility sufficient to enable the conduit 150 to be slid through a body lumen along an endoscope without unduly traumatizing tissue. Furthermore, those skilled in the art will understand that the frictional engagement of adjacent elements 100 may be adjusted to vary a degree of flexibility of the conduit 150 along its length in any desired pattern. For example, a distal end portion of the conduit 150 may be formed with enhanced flexibility to enable this distal end portion to follow the full range of motion of a steerable distal tip of an endoscope while a proximal portion of the conduit 150 shows an increased resistance to bending.

In the exemplary embodiment, one or both of the male portion 104 and the female portion 102 is preferably formed of a material which is plastically deformable to aid in assembling the conduit 150. That is, such a material allows either or both of the male portion 104 and the female portion 102 to deflect as the male portion 104 is inserted through the female portion 102 and then return to its original shape as a point of maximum diameter of the surface 108 aligns with a point of maximum diameter of the surface 110. Examples of suitable materials include plastics, such as, polypropylene, ABS, polystyrene, Nylon, etc.

Figure 3:
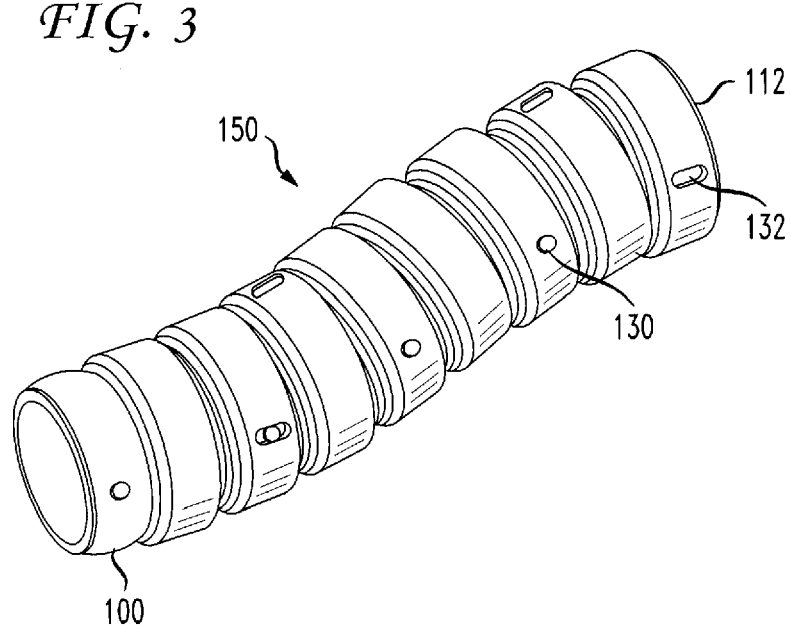
FIG. 3 is a perspective view showing multiple connected elements of a flexible conduit according to a first embodiment of the invention.
Figure 4:
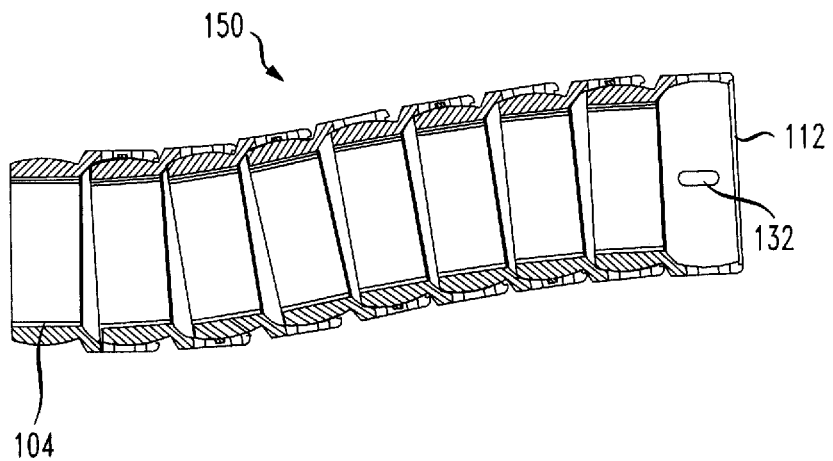
FIG. 4 is a partial cross-sectional side view of the flexible conduit of FIG. 3.
Figure 10:
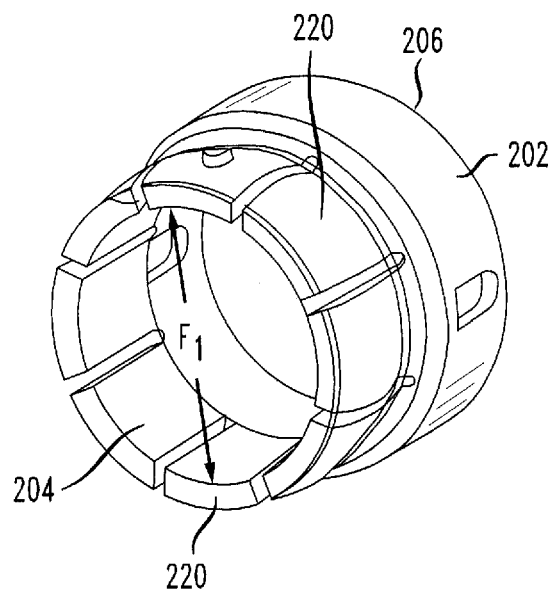
FIG. 10 is a perspective view showing forces applied to an element of a flexible conduit of FIG. 7.
Figure 11:
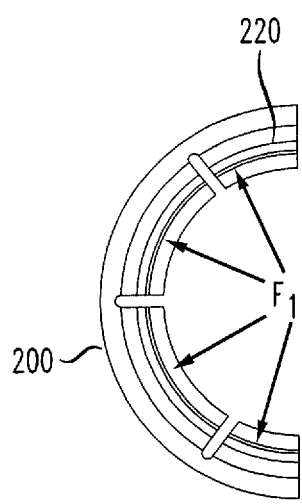
FIG. 11 is a partial cross-sectional view showing the element of FIG. 9.
Figure 12:
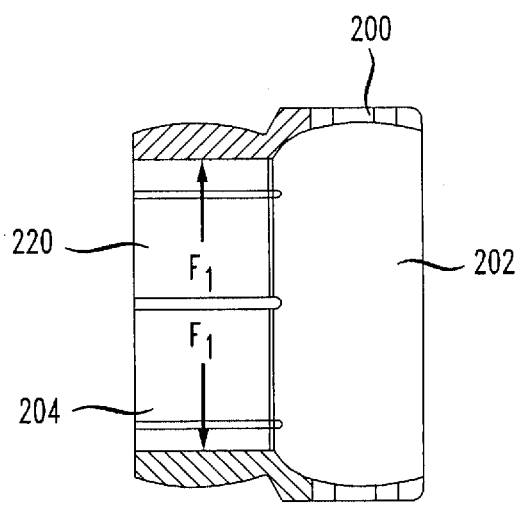
FIG. 12 is a side view of the element and forces shown in FIG. 9.

In one exemplary embodiment, the ball and socket joint between adjacent elements 100 may allow approximately 30 degrees of rotation of the elements 100 relative to one another about a line substantially perpendicular to the axis. However, as described above, greater flexibility may be desired in parts of the conduit 150 to, for example, allow for steering by the steerable distal tip of an endoscope (not shown). As shown in FIGS. 3 and 4, when many elements 100 are stacked together, a flexible conduit or catheter 150 having a solid but flexible structure is formed with a longitudinal lumen 112 extending therethrough. Those skilled in the art will understand that the rigidity of the conduit 150 may be varied significantly by changing any or all of materials, surface treatments, tolerances, etc. to achieve a rigidity desired for any given application. The radius of curvature may also be varied by altering the tolerances and size of the components as would be understood by those skilled in the art. In one exemplary embodiment, the conduit 150 is designed to permit radii of curvature of 2.75 inches and greater. However, those skilled in the art will understand that conduits for various applications may dictate different minimum radii of curvature. Depending on how a scope is anchored within a lumen and the stiffness of the conduit, a conduit such as the conduit 150 advanced thereover may act to straighten the endoscope or conform to the shape of the endoscope.

It may be useful to select a desired angular orientation of a distal end of the conduit 150 by transmitting a torque along the length of the conduit 150 from the proximal end of the conduit 150. According to the present invention, an optional linkage is provided between adjacent elements 100 that allows the conduit 150 to transmit a torque applied to its proximal end along its length to the distal end while retaining its longitudinal flexibility. That is, the conduit 150 is torsionally stiff while remaining longitudinally flexible. As shown in FIGS. 1 and 3, one or more protrusions 130 project radially outward from the outer surface 108 of the male portion 104, each mating with a corresponding receptacle 132 on the female portion 102. For example, a pair of protrusions 130 may be located one opposite points of the male portion 104, separated from one another by 180°. In one exemplary embodiment, the protrusion 130 is substantially cylindrical although other shapes may be utilized.

The receptacles 132 are formed on the female portion 102 at locations corresponding to the protrusion(s) 130 so that, when coupled to one another, each protrusion 130 of an element 100 is received within a receptacle 132 of an adjacent cylindrical element 100. For example, where the male portion 104 includes two projections 130 180° apart from one another, these projections 130 are preferably offset by 90° from the receptacles 132 of the same cylindrical element 100. When this first cylindrical element 100 is mated to an adjacent second cylindrical element 100, the projections 130 of the first element 100 are received in the receptacles 132 of the second element 100 with the second element 100 rotated 90° relative to the first element 100. As a chain of elements 100 is linked together, the individual elements 100 are each offset by 90° relative to the proximal and distal adjacent elements 100. Those skilled in the art will understand that the torsional stiffness of the conduit 150 is enhanced by selecting the dimensions of the projections 130 and the receptacles 132 so that little, if any, play is allowed in the circumferential direction while a desired degree of longitudinal flexibility is obtained by allowing axial movement of the projections 130 relative to the receptacles 132 within which they are received.

For example, where the projections 130 are substantially cylindrical, the receptacles 132 may be formed as slots, a length of which is selected to be greater than a diameter of the projections 130 by a predetermined amount (e.g., wherein the projections 130 have a diameter of approximately 0.127 cm. the receptacles 132 may have a length of approximately 0.254 cm.), while the width thereof (i.e., dimension in the circumferential direction) is selected to fit the diameter of the projections 130 with just enough clearance to allow the projections 130 to slide axially in the receptacles 132. This arrangement allows torque to be efficiently transmitted along the length of the conduit 150.

Those of skill in the art will understand that the details of the features and of the slots formed on the cylindrical elements 100 may be varied. For example, the position of the slots and protrusions may be interchanged, so that protrusions extending inward from the inner surface 110 are received in slots formed in the outer surface 108. Other shapes may be used to transmit a rotational force, such as ridges protruding from both elements, keyways, etc. According to the invention, any combination of features that prevents relative rotation of adjacent cylindrical elements 100 while permitting longitudinal flexibility may be used.

As shown in FIGS. 5-16, alternative embodiments of the present invention allow for dynamic adjustment of the stiffness of the conduit so that the conduit may be placed in a flexible state as it is slid along an endoscope and then stiffened to absorb forces applied as the endoscope is inserted further into the body lumen. According to the invention, application of a force directed radially outward within the lumen 112 forces the male portion 104 to exert a force on the female portion 102 within which it resides, thus increasing the friction between the outer surface 108 and the inner surface 110 of the adjacent elements 100. The increased frictional resistance between the adjacent elements 100 increases the longitudinal stiffness of the conduit 150. In cases where flexibility is desired, the radial force is reduced or withdrawn entirely to reduce the frictional resistance between adjacent elements 100.

As shown in FIGS. 5-11, an element 200 of a conduit 300 is formed substantially similarly to the elements 100 of the conduit 150 except that the male portion 204 is slotted to form a plurality of tabs 220 separated from one another by slits extending substantially parallel to the longitudinal axis of the conduit 300 enhancing the ability of the male portion 204 to flex radially outward from the axis.

Each of the cylindrical elements 200 comprises a female portion 202 and a male portion 204 joined to one another to form a unitary element 200. As with the elements 100, an inner surface 210 of the female portion 202 is sized and shaped to slidingly receive an outer surface 208 of the male portion 204 to form a ball and socket joint. A curve of the inner surface 210 of the female portion 202 and a curve of the outer surface 208 of the male portion 204 are shaped and sized to closely fit one another while allowing for rotation about lines substantially perpendicular to the axis. However, if desired, the elements 200 may be more loosely joined to one another than the elements 100 to form a conduit 300 which, in an unstressed state, is more flexible than the conduit 150. For example, the surfaces 208 and 210 may form parts of spheres (or any other suitable curves) with a diameter of the inner surface 208 exceeding that of the outer surface 210 by a tolerance amount selected to maintain adjacent ones of the elements 200 bonded to one another while allowing the desired rotation.

As described above, the male portion 204 is divided into a plurality of tabs 220 separated from one another by slits 222. The slits 222 provide a clearance so that the tabs 220 can deflect radially outward from the axis of the lumen 212 extending through each cylindrical element 200. The material forming the male portion 204 is preferably elastic so that, after being deflected by an external force, the tabs 220 return to their original shape and location. For example, as the male portion 204 of one element 200 is inserted into the female portion 202 of another element 200, the tabs 220 deflect inward and then return to their original shape as a point of maximum diameter of the surface 208 aligns with a point of maximum diameter of the surface 210. The curvature of the inner and outer surfaces 208, 210 serves to couple adjacent elements 200 together.

Those skilled in the art will understand that the number of slits 222 and of tabs 220 may be varied to achieve a desired degree of flexibility of the resulting conduit 300. The shape of the tabs 220 may also be varied with the tabs 220 of any element 200 being identical to one another or including two or more different shapes. For example, an exemplary embodiment comprises two slits defining two identical tabs. In another example, eight substantially identical tabs 220 are placed symmetrically around the longitudinal axis of the conduit. In yet another example, the tabs 220 are different from one another and may also be placed at variable intervals around the circumference of the element 200.

In one exemplary embodiment, the ball and socket joint between adjacent elements 200 allows about 30 degrees rotation of the elements relative to one another about a line substantially perpendicular to the axis. As shown in FIGS. 7 and 8, when many elements 200 are stacked together, a flexible conduit or catheter 300 having a solid but flexible structure is formed with a longitudinal lumen 212 extending substantially the length of the conduit 300. In addition, as described above, the flexibility of the conduit 300 may be varied along its length by any of the manners mentioned above in regard to the conduit 150 to achieve the same goals.

In addition, the conduit 300 may be made torsionally stiff through the inclusion of a linkage similar to that described above in regard to the conduit 150. As shown in FIGS. 5 and 7, one or more protrusions 230 project radially outward from the outer surface 208 of the male portion 204. In one exemplary embodiment, the protrusion 230 is substantially cylindrical although other shapes may be utilized. For example, a pair of protrusions 230 may be located one opposite points of the male portion 204, separated from one another by 180°.

A receptacle 232 is formed on the female portion 202 at a location corresponding to each protrusion 230 so that, when coupled to one another, each protrusion 230 of a cylindrical element 200 is received within a receptacle 232 of an adjacent cylindrical element 200. For example, where the male portion 204 includes two projections 230 180° apart from one another, these projections 230 are preferably offset by 90° from the receptacles 232 of the same cylindrical element 200. When this first cylindrical element 200 is mated to an adjacent second cylindrical element 200, the projections 230 of the first element 200 are received in the receptacles 232 of the second element 200 with the second element 200 rotated 90° relative to the first element 200. As a chain of elements 200 is linked together, the individual elements 200 are each offset by 90° relative to the proximal and distal adjacent elements 200. Those skilled in the art will understand that the torsional stiffness of the conduit 300 is enhanced by selecting the dimensions of the projections 230 and the receptacles 232 so that little, if any, play is allowed in the circumferential direction while a desired degree of longitudinal flexibility is obtained by allowing axial movement of the projections 230 relative to the receptacles 232 within which they are received.

For example, as described above where the projections 230 are substantially cylindrical, the receptacles 232 may be formed as slots, a length of which is selected to be greater than a diameter of the projections 230 by a predetermined amount, while the width thereof (i.e., dimension in the circumferential direction) is selected to fit the diameter of the projections 230 with just enough clearance to allow the projections 230 to slide axially in the receptacles 232. This arrangement allows torque to be efficiently transmitted along the length of the conduit 300.

Those of skill in the art will understand that the details of the features and of the slots formed on the cylindrical elements 200 may be varied. For example, the position of the slots and protrusions may be interchanged, so that protrusions extending inward from the inner surface 210 are received in slots formed in the outer surface 208. Other shapes may be used to transmit a rotational force, such as ridges protruding from both elements, keyways, etc. According to the invention, any combination of features that prevents relative rotation of adjacent cylindrical elements 200 while permitting longitudinal flexibility may be used.

The embodiments according to the present invention provide for the conduit to have a stiffness which can be dynamically adjusted by a user. Application of a force $F_1$ directed radially outward against the flexible tabs 220 causes the male portion 204 to press more firmly against the female portion 202 of an adjacent element 200 increasing the friction between the outer surface 208 and the inner surface 210. This impedes relative movement between the adjacent elements 200, increasing the longitudinal stiffness of the conduit 300. FIGS. 9-12 show a schematic representation of exemplary forces $F_1$ acting on the tabs 220 in the radial direction to stiffen the conduit 300.

Various methods of applying the adjustable radial force $F_1$ to the flexible tabs 220 may be used according to the invention, as will be described below. In one exemplary embodiment, the radial force $F_1$ is provided by an inflatable element (not shown) located radially inward of the tabs 220. The inflatable element (e.g., a balloon) is coupled to a supply of inflation fluid operable by the user to expand and deflate the inflatable element (not shown) so that a pressure in the inflatable element adjusts a magnitude of the force $F_1$ applied to the radially inner surfaces of the cylindrical element 200 and, specifically, the flexible tabs 220. As the exemplary female portion 202 is substantially rigid, it is not significantly affected while the flexible tabs 220 of the male portion 204 are deflected radially outward to press against the inner surface 210 of the adjacent element 200 to vary the force $F_1$ exerted on the flexible tabs 220 and the friction between the adjacent elements 200 to a desired level.

Figure 13:
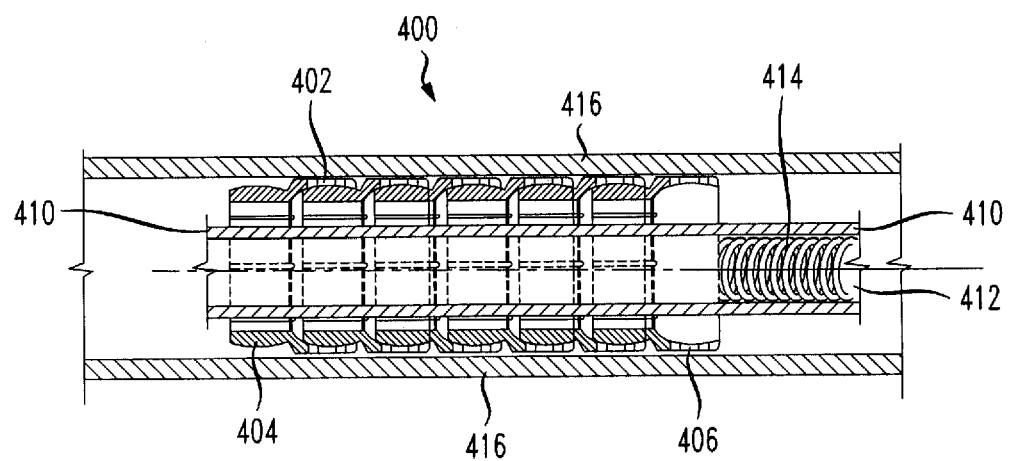
FIG. 13 is a side view showing another embodiment of a flexible conduit according to the invention, in a flexible state.
Figure 14:
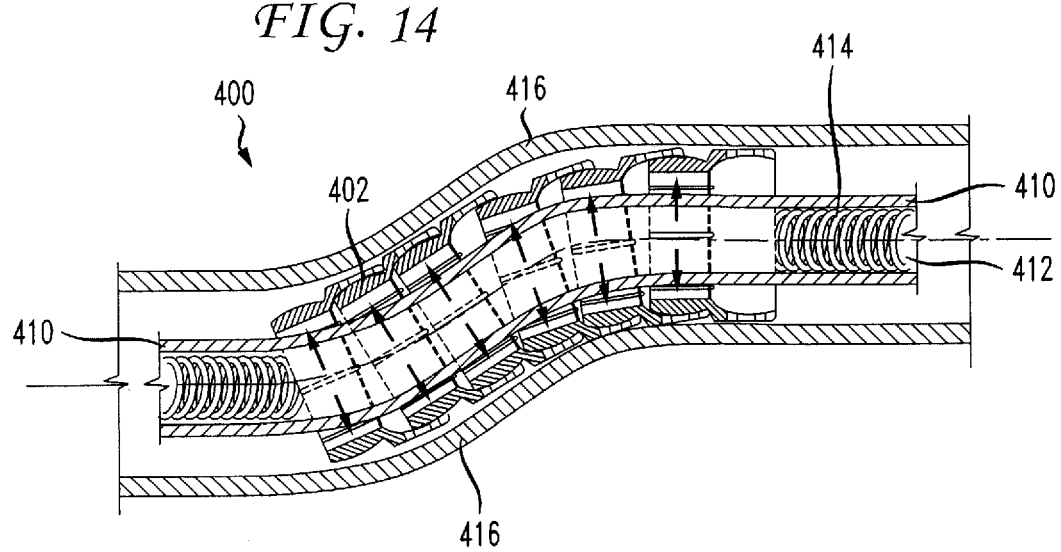
FIG. 14 is a side view showing the flexible conduit of FIG. 13 in a locked state.

In one exemplary embodiment shown in FIGS. 13 and 14, a conduit 400 is formed by joining together a plurality of elements 402 defining a lumen 412 that may be used, for example, to provide a passage for a scope or for other medical instruments. An optional coil spring 414 is placed in the lumen 412 to stabilize it, especially when in the flexible state shown in FIG. 13 and an outer cover 416 is placed over outer surfaces of the cylindrical elements 402, to protect the internal components of the conduit 400. For example, the outer cover 416 may comprise a braid and/or a PVC cover.

Each of the exemplary cylindrical elements 402 is formed of a male portion 404 and a contiguous female portion 406 similar to the male and female portions 204, 202, respectively, described above. As described above, the male portion 404 of one element 402 fits in the female portion 406 of an adjoining element 402. Both male and female portions, 404, 406 have opposing curved surfaces that slide one over the other, to form a ball and socket joint as described above in regard to the elements 200. The male portions 404 comprise tabs (not shown) that can be flexed radially outward to press against the female portions 406 and adjust a longitudinal stiffness of the conduit 400.

According to the invention, a hydraulic balloon sleeve 410 is disposed radially inward of inner surfaces of the cylindrical element 402, along the length of the variable conduit 400. FIG. 13 shows the conduit 400 in a flexible state in which the hydraulic balloon sleeve 410 is deflated and applies no outward force to the male elements 404. When an inflation fluid (e.g., water) is introduced under pressure to the hydraulic balloon sleeve 410 as shown in FIG. 18, outer surfaces of the balloon sleeve 410 move radially outward, flexing the male elements 404 radially outward against the female elements 406 to increase friction between adjacent elements 402 and enhance the rigidity of the conduit 400.

As would be understood by those skilled in the art, alternative embodiments of the invention may be devised, where the relative position of the male elements, female elements and inflatable elements are changed. For example, the inflatable element may be radially outside the cylindrical elements, such that inflating it produces a radially inward force which presses against the cylindrical elements. In this embodiment, the female elements may flex radially inward to engage substantially rigid male elements to increase a stiffness of the conduit. In other embodiments, a force may be applied to frictional elements that do not face in a radial direction, such that the deflection of the friction elements and/or the force acting on them is not in the radial direction.

Figure 15:
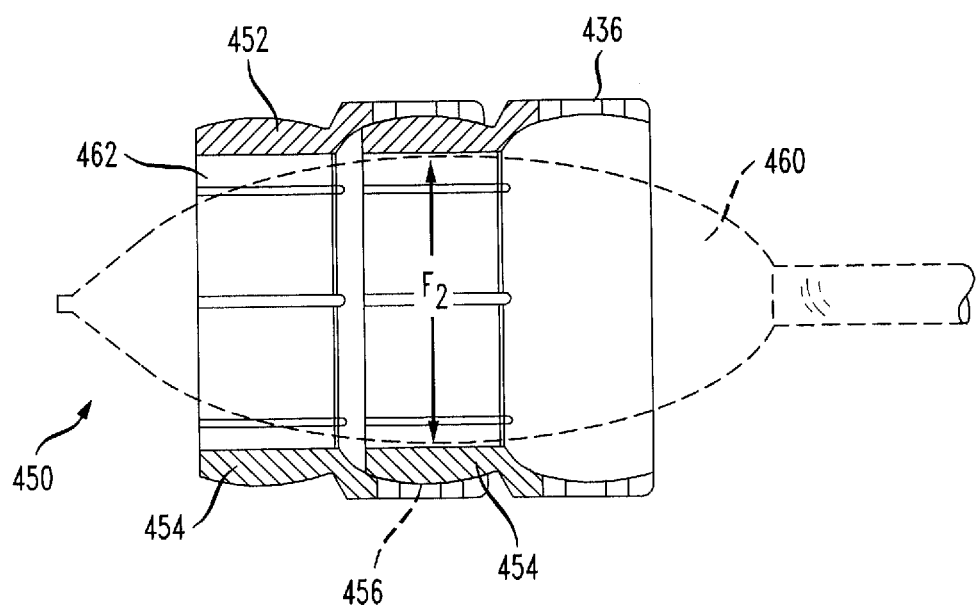
FIG. 15 is a side view showing yet another embodiment of an element of a flexible conduit according to the invention.
Figure 16:
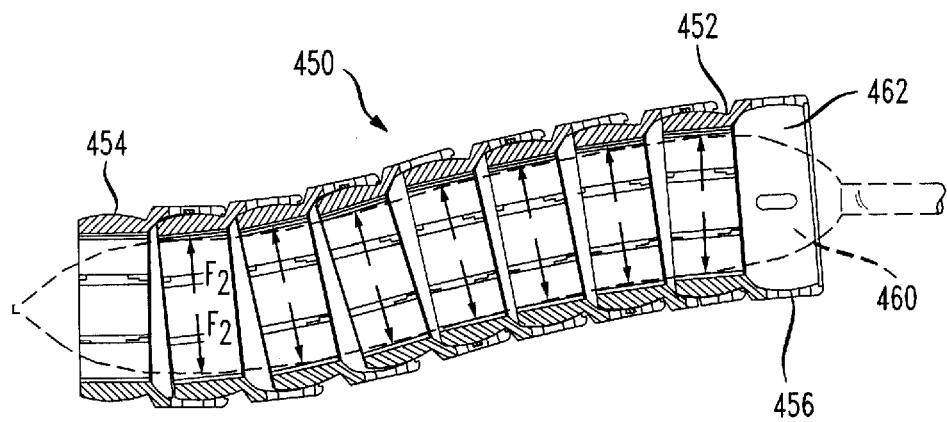
FIG. 16 shows a flexible conduit formed of the elements shown in FIG. 15.

As shown in FIGS. 15 and 16, a conduit 450 according to another embodiment of the invention comprises multiple substantially cylindrical elements 452 stacked together in a manner similar to that of the above-described embodiments. As described above, each cylindrical element 452 has a male portion 454 that fit in and interlocks with a female portion 456 of an adjacent element 452 to allow longitudinal flexing of the adjacent elements 452 relative to one another about an axis perpendicular to a longitudinal axis of the conduit 450 while preventing relative rotation between adjacent elements 452 about the longitudinal axis. The male and female portions 454, 456 slide relative to one another on opposite curved surfaces forming a ball and socket joint as described above.

A hydraulic or pneumatic inflatable element 460 disposed within the lumen 462 of the conduit 450 may be, for example, a balloon catheter or similar device. As shown in FIG. 15, when inflated, an inflatable element 460 applies a substantially radial force $F_2$ outward against the male portion 454 to frictionally engage the female portion 456 of the adjacent element 452 to rigidize the portion of the conduit 450. FIG. 16 shows a similar arrangement with a more extensive conduit 450 including a more elongated element 460 inflated with, for example, water, air or another fluid to apply radially outward force to the male portions 454 of a plurality of elements 452 to rigidize this portion of the conduit 450 in the same manner described above in regard to FIG. 15. Those skilled in the art will understand that the length of the rigidizable portions of the conduit 450 may be varied and that a single element 460 may rigidize a substantial portion of the length of the conduit 450, only a selected smaller portion or that multiple elements 460 may be employed to dynamically alter the rigidity of various sections of the conduit 450 independently of one another. In the mean time, the conduit 450 may optionally include one or more portions which are always relatively flexible (i.e., which are not acted on by inflation of an element 460) in any desired pattern.

Those skilled in the art will understand that any other suitable arrangement for imparting a radial force to deflect an element of such a ball and socket joint to selectively enhance the frictional engagement of adjacent elements may be employed without departing from the scope of the invention. For example, in place of an inflatable element, a spring like structure or mesh may be mechanically expanded and constricted. In addition, as described above, this force may be directed radially inward to deflect a radially outer element against a radially inner element or vice versa.

By varying a pressure at which the inflation fluid is supplied the stiffness of the conduit may be varied to a desired level up to and including levels required to resist forces to which the conduit is likely to be exposed in the environment within which it is to be deployed. That is, conduits according to the invention may be made stiff enough to retain their shape against anatomical forces to which they will likely be exposed as well as to resist bending forces applied thereto by flexible instruments such as endoscopes inserted therethrough. As would be understood by those skilled in the art, any conventional pump, compressor, storage device for pressurized fluid or other device may be used to provide the fluid used to inflate the expandable inflatable elements according to the invention.

The present invention has been described with reference to specific exemplary embodiments. Those skilled in the art will understand that changes may be made in details, particularly in matters of shape, size, material and arrangement of parts. Accordingly, various modifications and changes may be made to the embodiments. The specifications and drawings are, therefore, to be regarded in an illustrative rather than a restrictive sense.

The invention claimed is:

1. A flexible conduit, comprising:
a plurality of elements, wherein each element has a lumen, and the plurality of elements are coupled together with the lumens aligned to define a conduit lumen, the plurality of elements including:
a first element including a male portion and a female portion; and
a second element including a female portion sized to slidingly receive therewithin the male portion of the first element, an outer surface of the male portion of the first element being curved along a shape corresponding to a curve of an inner surface of the female portion of the second element; and
a force applying mechanism to apply a radial force to at least one of the plurality of elements to adjust a frictional force between the first element and the second element to adjust a stiffness of the flexible conduit.

2. The flexible conduit according to claim 1, wherein the force applying mechanism includes at least one of an inflatable element and a mechanical element.

3. The flexible conduit according to claim 2, wherein the inflatable element, when inflated, applies a radially outwardly directed force to the first element urging the first element radially outward into engagement with the second element.

4. The flexible conduit according to claim 3, wherein the radially outwardly directed force is applied to the male portion of the first element to urge the male portion of the first element radially outward into engagement with the female portion of the second element.

5. The flexible conduit according to claim 2, wherein the inflatable element is one of a balloon and an inflatable sleeve.

6. The flexible conduit according to claim 2, wherein the inflatable element, when inflated, produces a radially inwardly directed force to press the first element and the second element into engagement.

7. The flexible conduit according to claim 6, wherein the radially inwardly directed force is applied to the female portion of the second element to urge the female portion of the second element radially inward into engagement with the male portion of the first element.

8. The flexible conduit according to claim 1, further comprising a flexible sheath surrounding at least part of the first element and the second element to present a smooth exterior surface of the flexible conduit.

9. The flexible conduit according to claim 1, wherein at least one of the outer surface of the male portion and the inner surface of the female portion of the first element is surface treated to enhance a frictional coupling with a surface mated thereto.

10. The flexible conduit according to claim 1, wherein the outer surfaces of the male portions of the first element and the second element are formed as partially spherical surfaces having a first diameter, and wherein the inner surfaces of the female portions of the first element and the second element are formed as partially spherical surfaces having diameters greater than the first diameter.

11. The flexible conduit according to claim 1, further comprising a coil spring stabilizer disposed at least partially in the conduit lumen.

12. A flexible conduit, comprising:
a plurality of elements, wherein each element has a lumen, and the plurality of elements are coupled together with the lumens aligned to define a conduit lumen, the plurality of elements including:
a first element including a male portion and a female portion; and
a second element including a female portion sized to slidingly receive therewithin the male portion of the first element, an outer surface of the male portion of the first element being curved along a shape corresponding to a curve of an inner surface of the female portion of the second element;
a force applying mechanism to apply a radial force to at least one of the plurality of elements to adjust a frictional force between the first element and the second element to adjust a stiffness of the flexible conduit;
a first projection extending from one of the first element and the second element to mate with a first receptacle formed on the other of the first element and the second element to limit relative rotation therebetween about a longitudinal axis of the flexible conduit; and
a second projection extending from one of the first element and the second element mating with a second receptacle formed on the other of the first element and the second element, the second receptacle including a second slot having a length in a direction substantially parallel to the longitudinal axis of the flexible conduit selected to permit a desired degree of relative axial movement between the first element and the second element.

13. The flexible conduit according to claim 12, wherein the first receptacle includes a first slot having a length to permit a desired degree of relative axial movement between the first element and the second element.

14. A flexible conduit, comprising:
a plurality of elements, wherein each element has a lumen, and the plurality of elements are coupled together with the lumens aligned to define a conduit lumen, the plurality of elements including:
a first element including a male portion and a female portion; and
a second element including a female portion sized to slidingly receive therewithin the male portion of the first element, an outer surface of the male portion of the first element being curved along a shape corresponding to a curve of an inner surface of the female portion of the second element; and a force applying mechanism to apply a radial force to at least one of the plurality of elements to adjust a frictional force between the first element and the second element to adjust a stiffness of the flexible conduit;

wherein the male portion of the first element includes a plurality of flexible tabs separated from one another by slits extending substantially parallel to a longitudinal axis of the flexible conduit.

15. The flexible conduit according to claim 14, wherein the force applying mechanism applies the radial force to the plurality of tabs to flex the plurality of tabs radially outward.

* * * * *